United States Patent [19]
Kikumoto

[11] Patent Number: 5,925,760
[45] Date of Patent: Jul. 20, 1999

[54] METHOD FOR PREPARING $N^2$-ARYLSULFONYL-L-ARGININAMIDES

[75] Inventor: Ryoji Kikumoto, Tokyo, Japan

[73] Assignee: Mitsubishi Chemical Corporation, Tokyo, Japan

[21] Appl. No.: 08/904,555

[22] Filed: Aug. 4, 1997

[30] Foreign Application Priority Data

Aug. 7, 1996 [JP] Japan .................................. 8-208087

[51] Int. Cl.⁶ .................................................. C07D 215/36
[52] U.S. Cl. ........................... 546/172; 514/311; 514/314
[58] Field of Search ............................ 546/172; 514/314, 514/311

[56] References Cited

U.S. PATENT DOCUMENTS 4,101,653  7/1978  Okamoto ................................ 424/177

FOREIGN PATENT DOCUMENTS 0 008 746  3/1980  European Pat. Off. .
2 153 825  8/1985  United Kingdom .
WO96/29327  9/1996  WIPO .

*Primary Examiner*—D. Margaret M. Mach
*Attorney, Agent, or Firm*—Wenderoth, Lind & Ponack, L.L.P.

[57] ABSTRACT

A method for preparing $N^2$-(3-(a hydrogen atom or a lower alkyl)-8-quinolinesulfonyl)-$N^G$-nitro-L-arginine which comprises the step of condensing $N^G$-nitro-L-arginine and 3-(a hydrogen atom or a lower alkyl)-8-quinolinesulfonyl chloride. The method achieves an extremely efficient and high yield preparation of $N^2$-arylsulfonyl-L-arginineamides that are useful as active ingredients of medicaments. Also provided is a novel $N^2$-(3-(a hydrogen atom or a lower alkyl)-8-quinolinesulfonyl)-$N^G$-nitro-L-arginine compound which can be used as synthetic intermediate for the manufacture of (2R,4R)-4-methyl-1-[$N^2$-(3-methyl-1,2,3,4-tetrahydro-8-quinolinesulfonyl)-L-arginyl]-2-piperidinecarboxylic acid.

10 Claims, No Drawings

METHOD FOR PREPARING $N^2$-ARYLSULFONYL-L-ARGININAMIDES

BACKGROUND OF THE INVENTION

1. Field of the Invention

The present invention relates to a method for preparing $N^2$-arylsulfonyl-L-arginineamides which are useful as active ingredients of medicaments such as anti-thrombotic agents.

2. Related Art

The Japanese Patent Publication (KOKOKU) No. (Sho) 61-48829/1986 discloses, as Compound No. 6 in Table 1, (2R,4R)-4-methyl-1-[$N^2$-(3-methyl-1,2,3,4-tetrahydro-8-quinolinesulfonyl)-L-arginyl]-2-piperidine-carboxylic acid. As taught by the publication, this compound has highly specific inhibitory activity against thrombin that exists in a mammalian body, and is useful as an agent for therapeutic and preventive treatment of thrombosis, and as a platelet aggregation inhibitor. Monohydrate of this compound has been used as a selective anti-thrombotic agent for the treatment of chronic arterial occulsive diseases, cerebral thrombosis or other.

As a method for preparing the $N^2$-arylsulfonyl-L-arginineamides such as mentioned above, the method set out in the scheme below was known so far, as disclosed on pages 2 and 3 of the Japanese Patent Publication (KOKOKU) No. (Hei) 1-35000/1989 and on page 3 of the Japanese Patent Publication (KOKOKU) No. (Hei) 2-31055/1990. In the scheme, Ar represents 1,2,3,4-tetrahydro-8-quinolyl group whose 3-position is substituted with methyl group or ethyl group; Q represents 8-quinolyl group whose 3-position is substituted with methyl group or ethyl group; $R^1$ represents a hydrogen atom or a $C_{1-5}$ alkyl group; X represents a halogen atom; $R^2$ represents a hydrogen atom, a $C_{1-10}$ alkyl group, or a $C_{7-15}$ aralkyl group; at least one of R' and R" represents a protective group of the guanidino group; and R''' represents a protective group of the α-amino group.

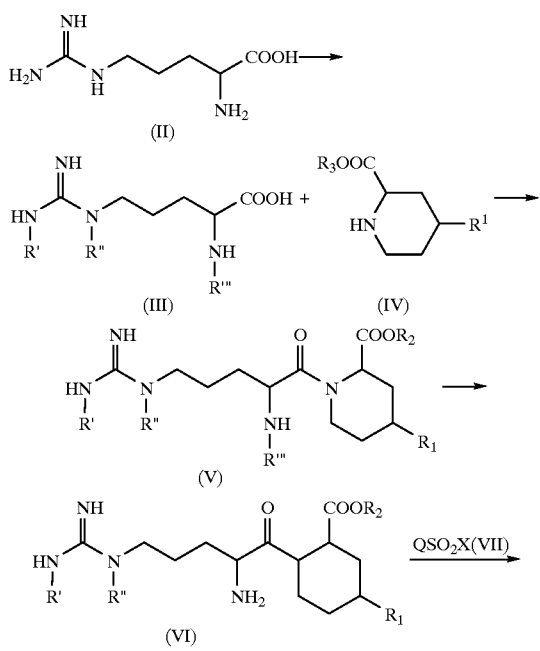

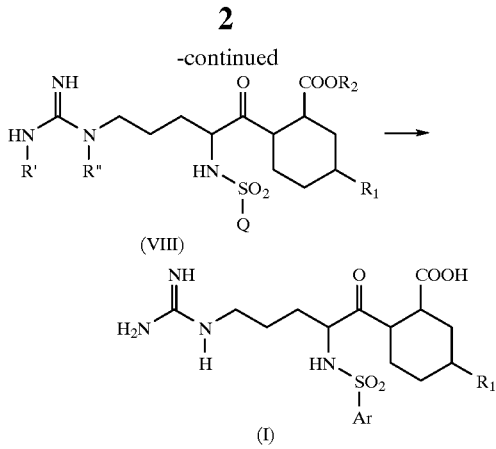

This method comprises the steps of condensing a piperidine-2-carboxylic acid derivative (Compound (IV) in the scheme) with an arginine derivative whose guanidino group and amino group on the α-carbon atom are appropriately protected (Compound (III) in the scheme); removing the protective group of the amino group on the α-carbon of the condensate obtained (Compound (V) in the scheme) and then allowing the resulting amino group react with a quinolinesulfonyl halide (Compound (VII) in the scheme); followed by removing the substituent on the guanidino group such as nitro group, and then reducing the quinolyl group and deblocking the carboxyl group to obtain the desired compound (Compound (I) in the scheme).

The Japanese Patent Publication (KOKOKU) No. (Sho) 61-48829/1986 discloses, as Example 2 on page 7, a specific process for preparing (2R,4R)-4-methyl-1-[$N^2$-(3-methyl-1,2,3,4-tetrahydro-8-quinolinesulfonyl)-L-arginyl]-2-piperidine-carboxylic acid according to the aforementioned method. The publication discloses that the ethyl ester of (2R,4R)-1-[$N^G$-nitro-$N^2$-(3-methyl-8-quinolinesulfonyl)-L-arginyl]-4-methyl-2-piperidine-carboxylic acid was prepared in the three-step process by using $N^G$-nitro-$N^2$-(tert-butoxycarbonyl)-L-arginine as a starting material, and the yield of step (A) was 74.5%.

The Japanese Patent Publication (KOKOKU) No. (Hei) 1-35000/1989 discloses the reaction scheme on pages 4 and 5 that relates to a process comprising the steps of condensing unprotected L-arginine (Compound (II) in the scheme) with an approximately equimolar amount of a quinolinesulfonyl halide (Compound (VII) in the scheme) to obtain $N^2$-quinolinesulfonyl-L-arginine (Compound (IX) in the scheme), and then allowing the resulting product react with the piperidine-2-carboxylic acid derivative (Compound (IV) in the scheme), followed by reducing the quinolyl group and deblocking the carboxyl group to obtain the desired compound, which will be shown in the scheme below. However, this method is not specifically demonstrated by any working example given in the publication, and moreover, it is impossible to obtain the desired compound with high selectivity, because the publication fails to teach any specific means to control the sulfonylation of the unprotected guanidino group which must be expected as an inevitable side reaction. Therefore, this method is of no significance to industrial applications. In addition, the publication neither teaches nor suggests a process of reacting an arginine having a protected guanidino group, e.g., Compound (III) shown in the scheme, with a quinolinesulfonyl halide according to the aforementioned method.

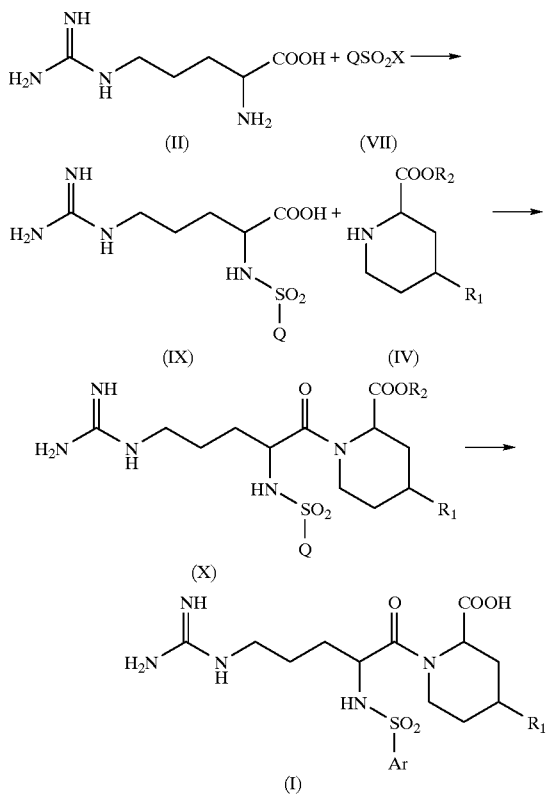

Therefore, an object of the present invention is to provide a method that enables efficient preparation of $N^2$-arylsulfonyl-L-arginineamides on an industrial scale. Another object of the present invention is to provide a synthetic intermediate compound which is useful for efficient preparation of $N^2$-arylsulfonyl-L-arginineamides.

SUMMARY OF THE INVENTION

The inventors of the present inventor conducted various researches to provide a more efficient method to prepare $N^2$-arylsulfonyl-L-arginineamides than those disclosed in the aforementioned patent publications. As a result, they found that each of the reactions can be completed with high efficiency by first condensing L-arginine having a nitro-protected guanidino group with a quinolinesulfonyl halide, and then allowing a piperidine-2-carboxylic acid derivative react with the α-amino group in the presence of a certain compound, thereby the process is successfully simplified and overall yield can be remarkably improved.

The present invention thus provides a method for preparing $N^2$(3-(a hydrogen atom or a lower alkyl)-8-quinolinesulfonyl)-$N^G$-nitro-L-arginine which comprises the step of condensing $N^G$-nitro-L-arginine and 3-(a hydrogen atom or a lower alkyl)-8-quinolinesulfonyl chloride. According to another embodiment of the present invention, there is provided a novel $N^2$-(3-methyl-8-quinolinesulfonyl)-$N^G$-nitro-L-arginine compound which is useful as a synthetic intermediate for the preparation of $N^2$-(3-(a hydrogen atom or a lower alkyl)-8-quinolinesulfonyl)-$N^G$-nitro-L-arginine compounds, preferably (2R,4R)-4-methyl-1-[$N^2$-(3-methyl-1,2,3,4-tetrahydro-8-quinolinesulfonyl)-L-arginyl]-2-piperidine-carboxylic acid, that are useful as active ingredients of medicaments.

According to a further embodiment of the present invention, there is provided a method for preparing a lower alkyl ester of 1-[$N^G$-nitro-$N^2$-(3-(a hydrogen atom or a lower alkyl)-8-quinolinesulfonyl)-L-arginyl]-4-methyl-2-piperidine-carboxylic acid which comprises the step of condensing $N^2$-(3-(a hydrogen atom or a lower alkyl)-8-quinolinesulfonyl)-$N^G$-nitro-L-arginine and a lower alkyl ester of 4-methylpiperidine-2-carboxylic acid. According to a still further embodiment of the present invention, there is provided a method for preparing a lower alkyl ester of 1-[$N^G$-nitro-$N^2$-(3-(a hydrogen atom or a lower alkyl)-8-quinolinesulfonyl)-L-arginyl]-4-methyl-2 -piperidine-carboxylic acid which comprises the steps of (a) preparing $N^2$-(3-(a hydrogen atom or a lower alkyl)-8-quinolinesulfonyl)-$N^G$-nitro-L-arginine by reacting $N^G$-nitro-L-arginine with 3-(a hydrogen atom or a lower alkyl)-8-quinolinesulfonyl chloride; and (b) condensing $N^2$-(3-(a hydrogen atom or a lower alkyl)-8-quinolinesulfonyl)-$N^G$-nitro-L-arginine obtained in the above step (a) with a lower alkyl ester of 4-methylpiperidine-2-carboxylic acid.

DETAILED EXPLANATION OF THE INVENTION

Best Mode for Carrying out the Invention

In the specification, the description of "3-(a hydrogen atom or a lower alkyl)" used in the names of compounds means that the substituent at the 3-position is either a hydrogen atom or a lower alkyl group. As to $N^2$-(3-(a hydrogen atom or a lower alkyl)-8-quinolinesulfonyl)-$N^G$-nitro-L-arginine, i.e., a novel compound provided by the present invention, a straight- or branched-chain $C_{1-4}$ alkyl group, preferably methyl group or ethyl group, and most preferably methyl group, may be used as the substituent at the 3-position.

$N^2$-(3-(a hydrogen atom or a lower alkyl)-8-quinolinesulfonyl)-$N^G$-nitro-L-arginine can be prepared by condensing $N^G$-nitro-L-arginine and 3-(a hydrogen atom or a lower alkyl)-8-quinolinesulfonyl chloride. An example of the method will be detailed in Examples of the specification. In general, the reaction may be carried out by dissolving nitroarginine in an aqueous solution of a base such as sodium hydroxide, and then adding 3-(a hydrogen atom or a lower alkyl)-8-quinolinesulfonyl chloride dissolved in a water-miscible organic solvent such as tetrahydrofuran or acetone to the above-obtained aqueous solution of nitroarginine. A base such as sodium carbonate may be optionally used in the reaction.

The reaction is preferably carried out under cooling, for example, at a temperature ranging from about 0 to 10° C. $N^G$-nitro-L-arginine and 3-(a hydrogen atom or a lower alkyl)-8-quinolinesulfonyl chloride, e.g., 3-methyl-8-quinolinesulfonyl chloride and 3-ethyl-8-quinolinesulfonyl chloride, that are used as starting materials are known compounds. For example, they can be prepared according to the method described in the Japanese Patent Publication (KOKOKU) No. (Hei) 4-984/1992, or alternatively, they can be readily obtained as commercially available products. $N^2$-(3-(a hydrogen atom or a lower alkyl)-8-quinolinesulfonyl)-$N^G$-nitro-L-arginine can be isolated and purified by applying ordinary post-treatments, and if required, by applying additional purification processes including chromatography and recrystallization. The above reaction can be conducted with an extremely high yield and results in little by-products. Therefore, a crude product contained in an extract or other material that is obtained by ordinary post-treatments, can usually be applied to the reaction in the next step without further isolation and purification of the resulting product.

$N^2$-arylsulfonyl-L-arginineamides which are useful as active ingredients of medicaments, preferably 4-methyl-1-[$N^2$-(3-(a hydrogen atom or a lower alkyl)-1,2,3,4-tetrahydro-8-quinolinesulfonyl)-L-arginyl]-2-piperidine-carboxylic acid and the like, can be efficiently prepared by using the aforementioned $N^2$-(3-(a hydrogen atom or a lower alkyl)-8-quinolinesulfonyl)-$N^G$-nitro-L-arginine. For example, 4-methyl-1-[$N^2$-(3-(a hydrogen atom or a lower alkyl)-1,2,3,4-tetrahydro-8-quinolinesulfonyl)-L-arginyl]-2-piperidine-carboxylic acid can be prepared in a high yield by the steps of condensing $N^2$-(3-(a hydrogen atom or a lower alkyl)-8-quinolinesulfonyl)-$N^G$-nitro-L-arginine with a lower alkyl ester of 4-methyl-2-piperidine-carboxylic acid to obtain a lower alkyl ester of 1-[$N^G$-nitro-$N^2$-(3-(a hydrogen atom or a lower alkyl)-8-quinolinesulfonyl)-L-arginyl]-4-methyl-2-piperidine-carboxylic acid; hydrolyzing the lower alkyl ester group of the resulting compound; and then subjecting the resulting carboxylic acid derivative to catalytic hydrogenation.

As lower alkyl ester groups that are comprised of the lower alkyl esters of the 4-methyl-2-piperidine-carboxylic acid used in the above reaction, for example, a straight- or branched-chain $C_{1-4}$ alkyl group, preferably methyl group or ethyl group, most preferably ethyl group, may be used. The aforementioned piperidine derivatives have two asymmetric carbon atoms, and accordingly, their optical isomers and diastereoisomers can exist. These isomers in pure forms may be used in the method of the present invention, or alternatively, any mixtures thereof can also be used. Where optically active isomers are used, their stereostructures are not particularly limited. For example, lower alkyl esters of (2R,4R)-4-methyl-2-piperidine-carboxylic acid may preferably used. Ethyl (2R,4R)-4-methyl-2-piperidine-carboxylate is most preferably used as the ester compound. These piperidine derivatives can be easily obtained, for example, according to the methods described in the Japanese Patent Publication (KOKOKU) Nos. (Sho) 61-25029/1986 and (Sho) 62-34035/1987, as well as in the Japanese Patent Unexamined Publication (KOKAI) No. (Hei) 2-212473/1990.

For the condensation of the aforementioned lower alkyl ester of 4-methyl-2-piperidine-carboxylic acid with $N^2$-(3-(a hydrogen atom or a lower alkyl)-8-quinolinesulfonyl)-$N^G$-nitro-L-arginine, any methods can be applied so far that they are applicable as methods for condensation between an amino group and a carboxyl group by dehydration, whose examples include acid halide methods, mixed acid anhydride methods, activated ester methods, and methods using condensing agents. As a preferred embodiment of the present invention, a method for the condensation using phosphorus oxychloride will be detailed in Examples. This reaction can be generally carried out in an organic solvent such as tetrahydrofuran at a temperature of not higher than 10° C., preferably not higher than 5° C., and most preferably not higher than 0° C., by adding phosphorus oxychloride dropwise to a solution of $N^2$-(3-(a hydrogen atom or a lower alkyl)-8-quinolinesulfonyl)-$N^G$-nitro-L-arginine, and then adding a lower alkyl ester of 4-methyl-2-piperidine-carboxylic acid and an appropriate base such as triethylamine successively to the reaction mixture.

Where condensing agents are used to carry out the reaction, the condensing agents are not particularly limited. For example, N',N'-dicycloalkylcarbodiimides such as N',N'-cyclohexylcarbodiimide (DCC); carbodiimide derivatives such as 1-ethyl-3-(3-dimethylaminopropyl) carbodiimide (EDAPC); or benzotriazole derivatives such as 1-hydroxybenzotriazole (HOBT) may be used. In addition, N-hydroxy derivatives, disulfide compounds, succinic acid compounds, phosphinic chloride compounds, oxalate derivatives, triarylphosphines, N-(a lower alkyl)-5-aryl-isooxazolium-3'-sulfonates, diheteroaryl diselenides, arylsulfonyl triazolides, 2-halo-1-(a lower alkyl)pyridinium halides, diarylphosphoryl azides, imidazole derivatives, dicarboxyimide derivatives and the like may be used.

Examples of agents for preparing activated esters that are used in the activated ester methods include, for example, an N-hydroxy compounds such as N-hydroxysuccinimide, 1-hydroxybenzotriazole, or N-hydroxy-5-norbornene-2,3-dicarboxyimide; disulfide compounds such as dipyridyl disulfide or the like. Where the carboxyl group is converted into an acid halide according to the acid halide method, for example, phosphorus pentachloride, thionyl chloride, oxalyl chloride or the like can be used as a halogenating agent. However, methods for condensation of the above compounds and reagents can be suitably chosen by those skilled in the art, and accordingly, they are not limited to those explained above.

By subjecting the lower alkyl ester of 1-[$N^G$-nitro-$N^2$-(3-(a hydrogen atom or a lower alkyl)-8-quinolinesulfonyl)-L-arginyl]-4-methyl-2-piperidine-carboxylic acid prepared as described above to hydrolysis and catalytic hydrogenation according to any one of methods that are known, per se, 4-methyl-1-[$N^2$-(3-(a hydrogen atom or a lower alkyl)-1,2, 3,4-tetrahydro-8-quinolinesulfonyl)-L-arginyl]-2-piperidine-carboxylic acid, preferably 4-methyl-1-[$N^2$-(3-methyl-1,2,3,4-tetrahydro-8-quinolinesulfonyl)-L-arginyl]-2-piperidine-carboxylic acid, more preferably (2R,4R)-4-methyl-1-[$N^2$-(3-methyl-1,2,3,4-tetrahydro-8-quinoline-sulfonyl)-L-arginyl]-2-piperidine-carboxylic acid, and most preferably (2R,4R)-4-methyl-1-[$N^2$-(3-methyl-1,2,3,4-tetrahydro-8-quinoline-sulfonyl)-L-arginyl]-2-piperidine-carboxylic acid monohydrate, can be prepared. The reaction may preferably be carried out, for example, according to the methods described in the steps (D) and (E) on pages 8 and 9 of the Japanese Patent Publication (KOKOKU) No. (Hei) 1-35000/1989, and the steps (D) and (E) on pages 7 and 8 of the Japanese Patent Publication (KOKOKU) No. (Sho) 61-48829/1986.

EXAMPLES

The present invention will be explained more specifically by referring to the following examples. However, the scope of the present invention is not limited to the examples.

(1) $N^G$-nitro-L-arginine (20 g) was dissolved in 25% aqueous solution of sodium hydroxide, and sodium carbonate (9.7 g) was added to the aqueous solution. To this reaction mixture, a solution of 3-methyl-8-quinolinesulfonyl chloride (27.4 g) in tetrahydrofuran (360 ml) was added dropwise under cooling. After completion of the dropwise addition, the reaction mixture was left at room temperature and stirred for two hours. The reaction mixture was adjusted to pH 2.7 with diluted hydrochloric acid under water-cooling, and then the solvent was evaporated under reduced pressure. Methanol (270 ml) was added to the residue and the solvent was again evaporated under reduced pressure and the residue was cooled. The resulting slurry mixture was filtered and the precipitates collected were washed with water to obtain $N^2$-(3-methyl-8-quinolinesulfonyl)-$N^G$-nitro-L-arginine (35 g).

Melting point 196–198° C. Angle of rotation $[a]_D^{24}$ +116° C. (c=1, 2N HCl). I.R. (KBr, $cm^{-1}$) 1700, 1650, 1330, 1170

(2) $N^2$-(3-methyl-8-quinolinesulfonyl)-$N^G$-nitro-L-arginine (35 g) was dissolved in tetrahydrofuran (360 ml)

and the solution was cooled to −10° C. To this solution, a solution of phosphorus oxychloride (19.5 g) in tetrahydrofuran (90 ml) was added dropwise at −10° C. A solution of ethyl (2R,4R)-4-methylpiperidine-2-carboxylate (20 g) in tetrahydrofuran (90 ml) was added dropwise to the reaction mixture at −10° C., and then triethylamine (24 g) was added dropwise at −10° C. After completion of the dropwise additions, the reaction mixture was stirred at −5° C. for one hour. After completion of the reaction, the reaction mixture was added with saturated brine (330 ml) and layers were separated to give a solution of ethyl (2R,4R)-1-[$N^G$-nitro-$N^2$-(3-methyl-8-quinolinesulfonyl)-L-arginyl]-4-methyl-2-piperidine-carboxylate in tetrahydrofuran. The overall yield of the above steps (1) and (2) was 78%.

(3) Monohydrate crystals of (2R,4R)-4-methyl-1-[$N^2$-(3-methyl-1,2,3,4-tetrahydro-8-quinolinesulfonyl)-L-arginyl]-2-piperidine-carboxylic acid were obtained from ethyl (2R,4R)-1-[$N^G$-nitro-$N^2$-(3-methyl-8-quinolinesulfonyl)-L-arginyl]-4-methyl-2-piperidine-carboxylate obtained in the above step (2) according to the method described in Examples (D) and (E) on page 7 of the Japanese Patent Publication (KOKOKU) No. (Hei)-2-31055/1990. IR spectrum of the resulting monohydrate crystals was found to be identical to that of the compound manufactured and sold under a non-proprietary name of "argatroban."

From these results, it can be readily understood that $N^2$-arylsulfonyl-L-arginineamides can be efficiently prepared on an industrial scale according to the method of the present invention. It can also be understood that $N^2$-(3-(a hydrogen atom or a lower alkyl)-8-quinolinesulfonyl)-$N^G$-nitro-L-arginine provided by the present invention is useful as a synthetic intermediate for efficient manufactures of $N^2$-arylsulfonyl-L-arginineamides which are useful as active ingredients of medicaments.

What is claimed is:

1. A method for preparing $N^2$-(3-(a hydrogen atom or a lower alkyl)-8-quinolinesulfonyl)-$N^G$-nitro-L-arginine which comprises the step of condensing $N^G$-nitro-L-arginine and 3-(a hydrogen atom or a lower alkyl)-8-quinolinesulfonyl chloride.

2. $N^2$-(3-(a hydrogen atom or a lower alkyl)-8-quinolinesulfonyl)-$N^G$-nitro-L-arginine.

3. A method for preparing a lower alkyl ester of 1-[$N^G$-nitro-$N^2$-(3-(a hydrogen atom or a lower alkyl)-8-quinolinesulfonyl)-L-arginyl]-4-methyl-2-piperidine-carboxylic acid which comprises the step of condensing $N^2$-(3-(a hydrogen atom or a lower alkyl)-8-quinolinesulfonyl)-$N^G$-nitro-L-arginine and a lower alkyl ester of 4-methylpiperidine-2-carboxylic acid.

4. The method according to claim 3, wherein the condensation is carried out in the presence of phosphorus oxychloride.

5. The method according to claim 3, wherein the ester compound is (2R,4R)-4-methylpiperidine-2-carboxylic acid ethyl ester.

6. The method according to claim 4, wherein the ester compound is (2R,4R)-4-methylpiperidine-2-carboxylic acid ethyl ester.

7. A method for preparing a lower alkyl ester of 1-[$N^G$-nitro-$N^2$-(3-(a hydrogen atom or a lower alkyl)-8-quinolinesulfonyl)-L-arginyl]-4-methyl-2-piperidine-carboxylic acid which comprises the steps of:

(a) preparing $N^2$-(3-(a hydrogen atom or a lower alkyl)-8-quinolinesulfonyl-$N^G$-nitro-L-arginine by reacting $N^G$-nitro-L-arginine with 3-(a hydrogen atom or a lower alkyl)-8-quinolinesulfonyl chloride; and (b) condensing the $N^2$-(3-(a hydrogen atom or a lower alkyl)-8-quinolinesulfonyl)-$N^G$-nitro-L-arginine obtained in the above step (a) with a lower alkyl ester of 4-methylpiperidine-2-carboxylic acid.

8. A method for preparing (2R,4R)-4-methyl-1-[$N^2$-(3-methyl-1,2,3,4-tetrahydro-8-quinolinesulfonyl)-L-arginyl]-2-piperidine-carboxylic acid which comprises the step of hydrolyzing the lower alkyl ester of 1-[$N^G$-nitro-$N^2$-(3-(a hydrogen atom or a lower alkyl)-8-quinolinesulfonyl)-L-arginyl]-4-methyl-2-piperidine-carboxylic acid obtained according to the method of claim 7, and then subjecting the resulting hydrolysate to catalytic hydrogenation.

9. The method according to claim 7, wherein 3-methyl-8-quinolinesulfonyl chloride is used as the 3-(a hydrogen atom or a lower alkyl)-8-quinolinesulfonyl chloride and ethyl (2R,4R)-4-methylpiperidine-2-carboxylate is used as the lower alkyl ester of 4-methylpiperidine-2-carboxylic acid.

10. The method according to claim 8, wherein 3-methyl-8-quinolinesulfonyl chloride is used as the 3-(a hydrogen atom or a lower alkyl)-8-quinolinesulfonyl chloride and ethyl (2R,4R)-4-methylpiperidine-2-carboxylate is used as the lower alkyl ester of 4-methylpiperidine-2-carboxylic acid.

* * * * *